US006617455B2

(12) United States Patent
De Wit

(10) Patent No.: US 6,617,455 B2
(45) Date of Patent: Sep. 9, 2003

(54) PROCESS FOR PREPARING MELAMINE FROM UREA

(75) Inventor: Nora Anna De Wit, Maastricht (NL)

(73) Assignee: DSM N.V., Heerlen (NL)

(*) Notice: Subject to any disclaimer, the term of this patent is extended or adjusted under 35 U.S.C. 154(b) by 0 days.

(21) Appl. No.: 10/210,876

(22) Filed: Aug. 2, 2002

(65) Prior Publication Data
US 2003/0040624 A1 Feb. 27, 2003

Related U.S. Application Data

(63) Continuation of application No. PCT/NL01/00047, filed on Jan. 24, 2001.

(30) Foreign Application Priority Data

Feb. 3, 2000 (NL) .............................................. 1014280

(51) Int. Cl.$^7$ ...................... C07D 251/60; C07D 251/62

(52) U.S. Cl. ........................................ 544/201; 544/203

(58) Field of Search .................................. 544/201, 203

(56) References Cited

FOREIGN PATENT DOCUMENTS

| EP | 114442 | 8/1984 |
|----|--------|--------|
| WO | 96 20933 | 7/1996 |

OTHER PUBLICATIONS

"The manufacture of non-fertilizer nitrogen products", NITROGEN, vol. 139, Sep. 1982, pp. 32–39.

*Primary Examiner*—Mukund J. Shah
*Assistant Examiner*—Venkataraman Balasubramanian
(74) *Attorney, Agent, or Firm*—Pillsbury Winthrop LLP

(57) ABSTRACT

Process for preparing melamine from urea at elevated temperature and in the presence of a catalyst, in which a gaseous product stream is obtained which is contacted with a liquid coolant in a cooling zone and that the temperature in the scrubbing section is lowered by applying an extra cooling step.

9 Claims, No Drawings

PROCESS FOR PREPARING MELAMINE FROM UREA

CROSS REFERENCE TO RELATED APPLICATION

This application is a continuation of International Application No. PCT/NL01/00047, filed Jan. 24, 2001, the disclosure of which is incorporated herein by reference in its entirety.

The invention relates to a process for preparing melamine from urea at elevated temperature and in the presence of a catalyst, in which a gaseous product stream is obtained which is contacted with a liquid coolant in a cooling zone.

A similar process is disclosed in for example WO-96/20933. This describes the preparation of melamine by supplying urea and ammonia to a reactor at a pressure of between 1.4 MPa and 2.0 MPa and a temperature high enough for virtually complete conversion of urea into melamine in the presence of a catalyst. In the process there is obtained a gas stream containing melamine, ammonia and carbon dioxide. In WO-96/20933 this gas stream is cooled with an aqueous coolant in what is known as a quench pipe with evolution of a vapour-liquid mixture, which mixture is virtually free from solid constituents. This vapour-liquid mixture is separated in this quench pipe into an aqueous melamine product stream and a vapour stream. The vapour stream from the quench pipe is virtually free from urea and melamine and consists essentially of ammonia, carbon dioxide and water vapour. The aqueous melamine product stream is virtually free from solids and contains dissolved ammonia and carbon dioxide. After the dissolved ammonia and carbon dioxide are removed with the aid of steam in a stripping section, the aqueous melamine product stream is passed to the melamine purification where the melamine is recovered. In this stripping section evolves also a vapour stream consisting essentially of ammonia, carbon dioxide and water vapour. The vapour stream from the quench pipe, together with the vapour stream from the stripping section, is scrubbed in a scrubbing section with an aqueous solution (mother liquor) from the melamine purification in order to remove melamine residues still present in the vapour stream. This aqueous solution may contain ammonia, carbon dioxide and melamine. The quench pipe and scrubbing section make up the cooling zone in the process according to WO-96/20933. Next, the gas stream from the scrubbing section is passed to an absorption zone where it is contacted with an aqueous ammonia stream and liquid ammonia, in which process there is obtained a solution of concentrated aqueous ammonia and carbon dioxide (carbamate solution) and ammonia vapour virtually free from water and carbon dioxide. In WO-96/20933, this ammonia vapour is condensed and partly returned to the absorption zone, the remainder after evaporation being used as fluidization gas for the reactor. The aqueous solution from the scrubbing section is passed to the quench pipe and used as coolant there.

The concentrated aqueous carbamate solution from the absorption zone, which WO-96/20933 reports contains 20–35% by weight of water, is for example supplied to a urea plant. Thus, in WO-96/20933 the gas mixture coming from the reactor is cooled with the mother liquor from the melamine purification, which liquor is passed to the quench pipe via the scrubbing section.

WO-96/20933 states that the water content of the carbamate solution from the absorption zone is so low, i.e. 20–35% by weight, that a concentration step, in which water is removed from the carbamate solution, is not needed before the carbamate solution is supplied to a urea plant.

Experiments carried out by the applicant in accordance with the process described in WO-96/20933 indicate, however, that it is advantageous to remove water from the carbamate solution if the aim is to operate the combination of melamine plant and urea plant in the most economical manner.

In a melamine plant water is used inter alia as a component of the liquid coolant. A proportion of the water eventually ends up in the carbamate solution from the absorption zone which is supplied to for example a urea plant.

Experiments and calculations by the applicant also indicate that in the process according to WO-96/20933 the exported amount of water is about 2.5 tons of water per ton of melamine. In an economically optimum process, such as the Stamicarbon process described in Nitrogen No. 139, September/October 1982, pp 32–39, the exported amount of water is about 0.5–1.0 ton of water per ton of melamine.

The aforementioned tons of water per ton of melamine may be converted to a water concentration in the carbamate solution from the absorption zone, if the $NH_3/CO_2$ ratio of the carbamate solution exported is determined. If the plant according to WO-96/20933 is operated in an economically optimum manner, this ratio is minimum, for example 1.3 kg of $NH_3$ per kg of $CO_2$. This means that the water concentration in the carbamate solution from the absorption zone in the process according to WO-96/20933 is 45–50% by weight. In the aforementioned Stamicarbon process this is only 20–25% by weight.

For supplying this 45–50% by weight of water-containing carbamate stream to a urea plant it is economically attractive to further concentrate the carbamate solution by removing water from this solution. The drawback hereof is that this entails additional investments and that the process becomes more costly due to increased usage of steam, cooling water and electricity.

It has been found that this drawback can be overcome by lowering the temperature in the scrubbing section by applying an extra cooling step. This results in the carbamate solution from the absorption zone having a lower water content than the carbamate solution from the absorption zone described in WO 96/20933.

The liquid coolant applied in the cooling zone preferably consists of an aqueous carbamate solution composed of mother liquor from the melamine purification (backend section) to which may be added ammonia, carbon dioxide and water condensed in the cooling zone.

Cooling in the scrubbing section reduces the water concentration in the liquid coolant. As a result of the reduction in the water content of the liquid coolant, a more concentrated carbamate solution is obtained in the absorption zone, which solution is suitable for use in a urea plant without the need to use an extra concentration step.

It has also been found that in the process of the invention the water content of the concentrated carbamate solution from the absorption zone eventually amounts to 20–35% by weight.

In a first embodiment, the temperature in the scrubbing section is lowered by passing the liquid from the scrubbing section to a heat exchanger, cooling the liquid in the heat exchanger with the aid of a liquid coolant, for example cooling water, and then returning the cooled liquid to the cooling zone. It is also possible to cool both the liquid stream coming from the scrubbing section and the gas stream and to return a proportion of the condensed gas phase to the cooling zone. In that case, too, a concentrated aqueous carbamate solution with a low water content is obtained from the absorption zone. The dilute carbamate solution obtained here from the condenser installed ahead of the absorption zone may then optionally be used as liquid coolant in the cooling zone.

In a second embodiment, a proportion of the heat is discharged by cooling the mother liquor from the melamine purification before the mother liquor is passed to the scrubbing section. A further temperature decrease may be obtained by application of the first embodiment.

The liquid from the scrubbing section is cooled, as a result of which the temperature in the scrubbing section is reduced by at least 5° C., in particular at least 10° C. This causes the temperature in the scrubbing section to decrease to 100–150° C. The temperature decrease in the scrubbing section can also be accomplished by reducing the temperature of the mother liquor from the melamine purification before it is returned to the cooling zone. This, too, results after the absorption step in a concentrated aqueous carbamate solution that can be supplied to a urea plant direct.

Furthermore, it has been found that the process of the invention is particularly suitable in what is known as gas-phase melamine plants which operate at a pressure of 0.6–2.5 MPa, more particularly at pressures of between 0.7 MPa and 2.2 MPa.

The invention may also be applied for modifying existing melamine plants.

The invention is illustrated by the following examples.

EXAMPLES I–III

Melamine was prepared in a cylindrical fluidized bed with an inside diameter of 1 meter and a height of 15 m. The catalyst was fluidized by introducing ammonia through a gas distribution plate and was heated by heat exchanger tubes in the reactor through which molten salt flowed. Liquid urea was sprayed into the reactor with the aid of a two-phase sprayer using ammonia as atomizing gas. The reactor was operated at 390° C. and a total pressure of 0.7 MPa (Example I), 1.7 MPa (Example II) and 2.0 MPa (Example III). Urea was sprayed at the rate of 1.4 tons/hour with 0.7 ton of ammonia per hour via the two-phase sprayers. Ammonia was supplied through the fluidization plate at the rate of 0.7 ton/hour. The conversion of water-free urea to melamine relative to equilibrium was higher than 98%. The gas stream from the reactor contained $NH_3$, $CO_2$, melamine vapour and traces of by-products and was cooled in the quench pipe with liquid coolant. The water content of the liquid coolant was reduced by cooling a dilute aqueous carbamate solution from the scrubbing section. The temperature in the scrubbing section was lowered here to the temperature stated in Table 1. This cooling was effected in a heat exchanger with the aid of cooling water whereupon the cooled liquid was returned to the scrubbing section. The carbamate stream coming from the absorption zone was supplied to the adjacent urea plant direct. The water concentration in this carbamate stream is given in Table 1.

COMPARATIVE EXAMPLE A

Analogously to Examples I–III, melamine was prepared except that the temperature in the scrubbing section was not lowered. The carbamate stream coming from the absorption zone was too dilute for it to be supplied to a urea plant without an intermediate step. Refer to Table 1.

TABLE 1

| Example | I | II | III | A |
|---|---|---|---|---|
| Pressure in Mpa | 0.7 | 1.7 | 2.0 | 1.7 |
| Temperature in scrubbing section in ° C. | 110 | 130 | 135 | 158 |
| Water content of carbamate from absorption zone in % by weight | 29 | 26 | 25 | 49 |
| Amount of exported water in kg per kg of melamine | 0.95 | 0.77 | 0.74 | 2.5 |

What is claimed is:

1. Process for preparing melamine from urea at elevated temperature and in the presence of a catalyst, in which a gaseous product stream is obtained which is contacted with a liquid coolant in a cooling zone, said process comprising further lowering the temperature in the scrubbing section by applying an extra cooling step.

2. Process according to claim 1, wherein the temperature in the scrubbing section is lowered by passing the liquid from the scrubbing section to a heat exchanger, cooling the liquid in the heat exchanger with the aid of a liquid coolant and then returning the cooled liquid to the cooling zone.

3. Process according to claim 1, wherein the temperature in the scrubbing section is reduced by at least 5° C.

4. Process according to claim 3, wherein the temperature in the scrubbing section is reduced by at least 10° C.

5. Process according to claim 1, wherein the gas coming from the reactor has a pressure of between 0.6 and 2.5 MPa.

6. Process according to claim 5, wherein the gas coming from the reactor has a pressure of between 0.7 and 2.2 MPa.

7. A method for modifying an existing melamine plant comprising applying the process according to claim 1.

8. Process according to claim 1, wherein melamine produced from urea is subjected to purification and a mother liquor is recovered from the melamine purification, said process further comprising cooling the mother liquor prior to the scrubbing section and using the cooled mother liquor to effect scrubbing in the scrubbing section.

9. Process for preparing melamine from urea at elevated temperature and in the presence of a catalyst, in which a gaseous product stream is obtained which is contacted with a liquid coolant in a cooling zone, and in which a mother liquor is recovered from melamine purification, said process comprising cooling the mother liquor prior to the scrubbing section and using the cooled mother liquor to effect scrubbing in the scrubbing section.

* * * * *